US012805901B2

(12) United States Patent
Yamamoto et al.

(10) Patent No.: US 12,805,901 B2
(45) Date of Patent: Nov. 24, 2026

(54) PUNCTURE NEEDLE, CATHETER ASSEMBLY, AND VASCULAR PUNCTURE SYSTEM

(71) Applicant: TERUMO KABUSHIKI KAISHA, Tokyo (JP)

(72) Inventors: Shota Yamamoto, Mitaka (JP); Takayuki Yokota, Chuo (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 979 days.

(21) Appl. No.: 17/939,899

(22) Filed: Sep. 7, 2022

(65) Prior Publication Data

US 2023/0000520 A1 Jan. 5, 2023

Related U.S. Application Data

(63) Continuation of application No. PCT/JP2021/009003, filed on Mar. 8, 2021.

(30) Foreign Application Priority Data

Mar. 12, 2020 (JP) ................................ 2020-042813

(51) Int. Cl.

*A61B 17/34* (2006.01)
*A61B 90/13* (2016.01)
*A61M 25/06* (2006.01)

(52) U.S. Cl.

CPC ..... *A61B 17/3403* (2013.01); *A61M 25/0606* (2013.01); *A61B 90/13* (2016.02); *A61M 2205/583* (2013.01)

(58) Field of Classification Search

CPC ... A61B 17/3403; A61B 90/13; A61B 5/1076; A61B 5/1079; A61B 5/489;

(Continued)

(56) References Cited

U.S. PATENT DOCUMENTS

2002/0099341 A1* 7/2002 Nakagami ........... A61M 5/3275 604/268
2018/0207356 A1 7/2018 Joseph et al.

FOREIGN PATENT DOCUMENTS

EP 1 258 261 A1 11/2002
JP 2009-233007 A 10/2009

(Continued)

OTHER PUBLICATIONS

International Searching Authority, "Written Opinion," issued in connection with International Patent Application No. PCT/JP2021/009003, dated May 11, 2021 with English translation.

(Continued)

*Primary Examiner* — Theodore J Stigell
(74) *Attorney, Agent, or Firm* — Foley & Lardner LLP

(57) ABSTRACT

A medical puncture needle includes: a metal needle body formed in a tubular shape and including: a blade surface formed at a distal end portion of the needle body, a first transmission window configured to transmit light, and a second transmission window configured to transmit light transmitted through the first transmission window. The second transmission window is located on a proximal end side relative to the blade surface. The first transmission window and the second transmission window are shifted from each other in a circumferential direction of the needle body.

9 Claims, 12 Drawing Sheets

(58) Field of Classification Search
CPC .......... A61B 5/6848; A61B 2090/3979; A61B 2090/373; A61M 25/0606; A61M 2205/583; A61M 25/065; A61M 5/158; A61N 2005/063
See application file for complete search history.

(56) References Cited

FOREIGN PATENT DOCUMENTS

| | | | |
|---|---|---|---|
| JP | 2012-532682 | A | 12/2012 |
| JP | 2013-009949 | A | 1/2013 |
| JP | 2018-171231 | A | 11/2018 |
| WO | WO-2014/061030 | A2 * | 4/2014 |
| WO | WO-2018/202806 | A1 | 11/2018 |

OTHER PUBLICATIONS

International Searching Authority, "International Search Report," issued in connection with International Patent Application No. PCT/JP2021/009003, dated May 11, 2021.
International Searching Authority, "Written Opinion," issued in connection with International Patent Application No. PCT/JP2021/009003, dated May 11, 2021.

* cited by examiner

PUNCTURE NEEDLE, CATHETER ASSEMBLY, AND VASCULAR PUNCTURE SYSTEM

CROSS REFERENCE TO RELATED APPLICATIONS

This is a bypass continuation of PCT Application No. PCT/JP2021/009003, filed on Mar. 8, 2021, which claims priority to Japanese Application No. JP2020-042813, filed on Mar. 12, 2020. The contents of these applications are hereby incorporated by reference in their entireties.

BACKGROUND

The present disclosure relates to a puncture needle, a catheter assembly, and a vascular puncture system.

A puncture needle such as an indwelling needle includes, for example, a metal needle body formed in a tubular shape (see JP 2009-233007 A). In addition, in recent years, a technique has been developed for visualizing the running of a blood vessel in a living body by an image obtained by receiving transmitted light of near-infrared light with which the living body is irradiated.

SUMMARY

In the metal needle described above, the metal needle body does not transmit near-infrared light. Therefore, the positional relationship between the needle body and the blood vessel in the living body can be visualized by the image (transmitted light image) obtained by receiving the transmitted light of the light (for example, near-infrared light) with which the living body punctured with the needle body is irradiated. However, the transmitted light image indicates the planar positional relationship between the needle body and the blood vessel, and does not indicate the positional relationship between the needle body and the blood vessel in the depth direction. Therefore, a user cannot be aware of whether the needle body is located in the blood vessel based on the transmitted light image.

Embodiments of the present disclosure have been developed in view of such problems, and an object of certain embodiments is to provide a puncture needle, a catheter assembly, and a vascular puncture system capable of allowing a user to recognize when a needle body is located in a blood vessel based on a transmitted light image.

According to a first aspect of the present disclosure, a medical puncture needle includes a metal needle body formed in a tubular shape, in which the needle body includes a blade surface formed at a distal end portion of the needle body, a first transmission window configured to transmit light, and a second transmission window configured to transmit light transmitted through the first transmission window, the second transmission window is located on a proximal end side relative to the blade surface, and the first transmission window and the second transmission window are shifted from each other in a circumferential direction of the needle body.

According to a second aspect of the present disclosure, a catheter assembly includes the above-described puncture needle and a catheter shaft having a lumen through which the needle body is inserted.

According to a third aspect of the present disclosure, a vascular puncture system includes the above-described puncture needle, an irradiation unit configured to irradiate a living body punctured with the needle body with the light; and a light receiving unit configured to receive transmitted light transmitted through the living body.

According to certain embodiments of the present invention, light with which the living body punctured with the needle body is irradiated is transmitted through the first transmission window and is guided to the lumen of the needle body. When the needle body is not located in the blood vessel and the blood does not flow into the lumen of the needle body, the light guided from the first transmission window into the lumen of the needle body is transmitted through the second transmission window and led to the outside of the needle body. Therefore, the user can visually recognize the second transmission window in the needle body in the transmitted light image. On the other hand, when the needle body is located in the blood vessel and the blood flowing into the lumen of the needle body covers the second transmission window, the light guided from the first transmission window to the lumen of the needle body is absorbed by the blood and thus is not transmitted through the second transmission window. Therefore, the appearance of the second transmission window of the needle body changes in the transmitted light image (the second transmission window is invisible or the second transmission window is difficult to see). Therefore, the user can recognize when the needle body is located in the blood vessel based on the transmitted light image.

DETAILED DESCRIPTION

Hereinafter, preferred embodiments of a puncture needle, a catheter assembly, and a vascular puncture system according to the present disclosure will be described with reference to the accompanying drawings.

Figure 1:
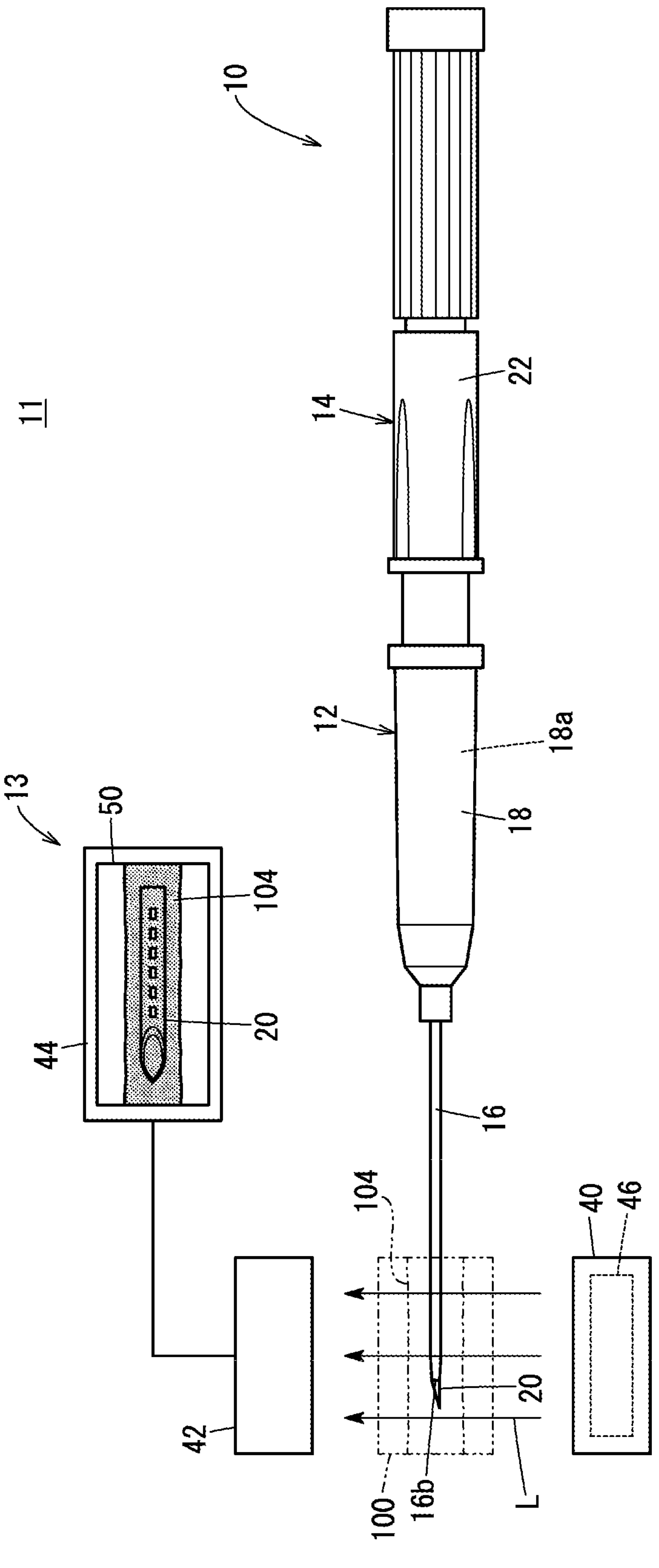
FIG. 1 is a schematic configuration diagram of a vascular puncture system according to an embodiment of the present invention.

As illustrated in FIG. 1, a vascular puncture system 11 according to an embodiment of the present disclosure includes a catheter assembly 10 configured to puncture a blood vessel 104 of a living body 100, and a visualization device 13 for visualizing the blood vessel 104 and the catheter assembly 10 in the living body 100.

Figure 2:
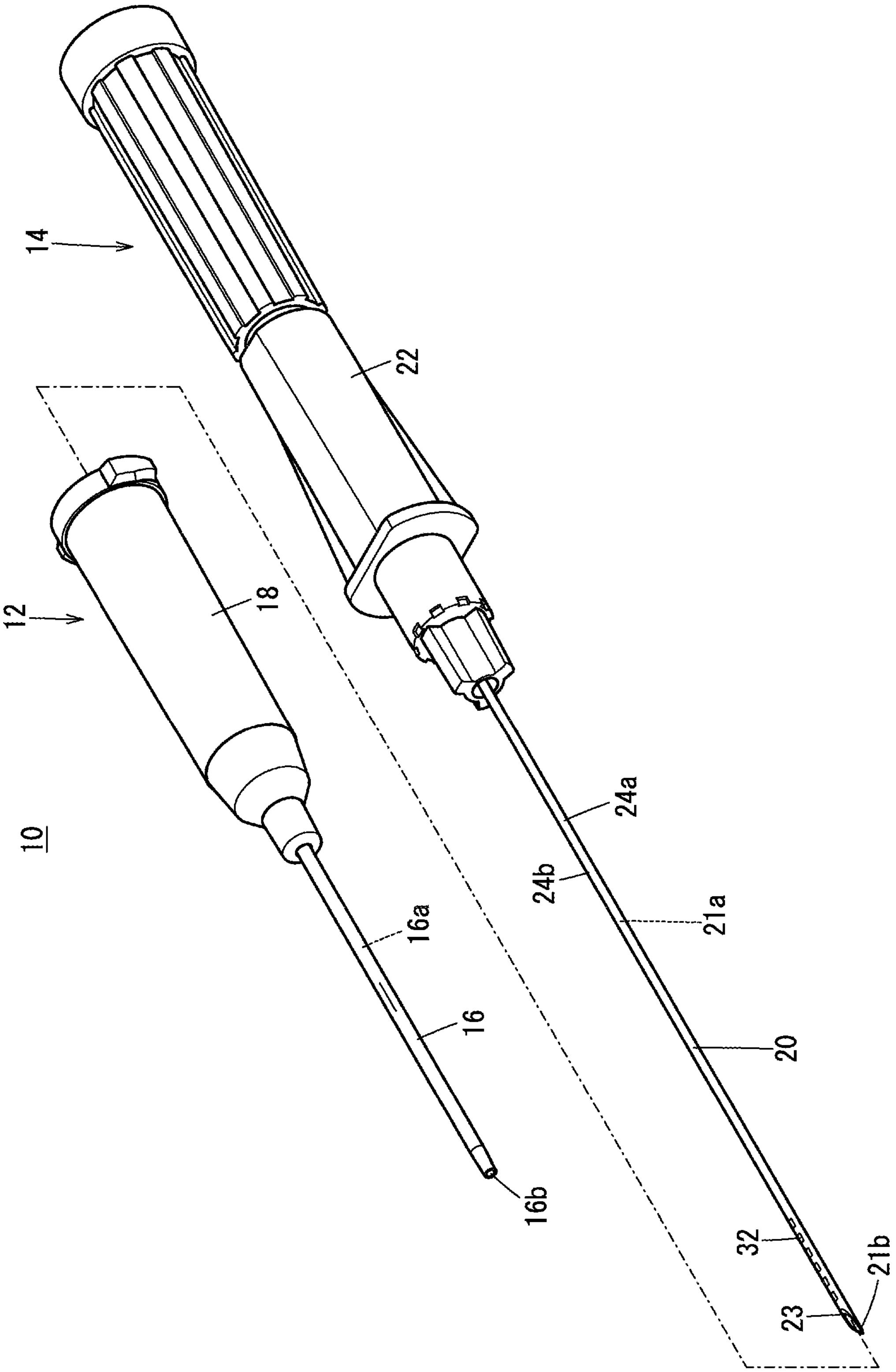
FIG. 2 is an exploded perspective view of the catheter assembly of FIG. 1.

The catheter assembly 10 is configured as an indwelling needle for administering an infusion (drug) into the blood vessel 104 of a patient (living body 100). However, the catheter assembly 10 is not limited to one that administers a drug. As illustrated in FIGS. 1 and 2, the catheter assembly 10 includes a catheter member 12 and a puncture needle 14. The catheter member 12 includes a catheter shaft 16 and a catheter hub 18 provided at a proximal end portion of the catheter shaft 16.

The catheter shaft 16 is a tubular member having flexibility and capable of being continuously inserted into the blood vessel 104 of the patient. The catheter shaft 16 has a lumen 16*a* extending along the axial direction over the entire length thereof. The catheter shaft 16 has at its distal end a distal end opening 16*b* communicating with the lumen 16*a*.

A constituent material of the catheter shaft 16 is not particularly limited, but a resin material having transparency, particularly a soft resin material is suitable, and examples thereof include a fluorine-based resin such as polytetrafluoroethylene (PTFE), ethylene-tetrafluoroethylene copolymer (ETFE), and perfluoroalkoxy fluorine resin (PFA), an olefin-based resin such as polyethylene and polypropylene or a mixture thereof, polyurethane, polyester, polyamide, polyether nylon resin, a mixture of an olefin-based resin and an ethylene-vinyl acetate copolymer, and the like.

The catheter hub 18 is formed in a hollow shape (cylindrical shape). The catheter hub 18 is preferably made of a material harder than the catheter shaft 16. A constituent material of the catheter hub 18 is not particularly limited, but for example, thermoplastic resins such as polypropylene, polycarbonate, polyamide, polysulfone, polyarylate, a methacrylate-butylene-styrene copolymer, polyurethane, an acrylic resin, and an ABS resin can be suitably used.

Figures 3A, 3B, 3C:
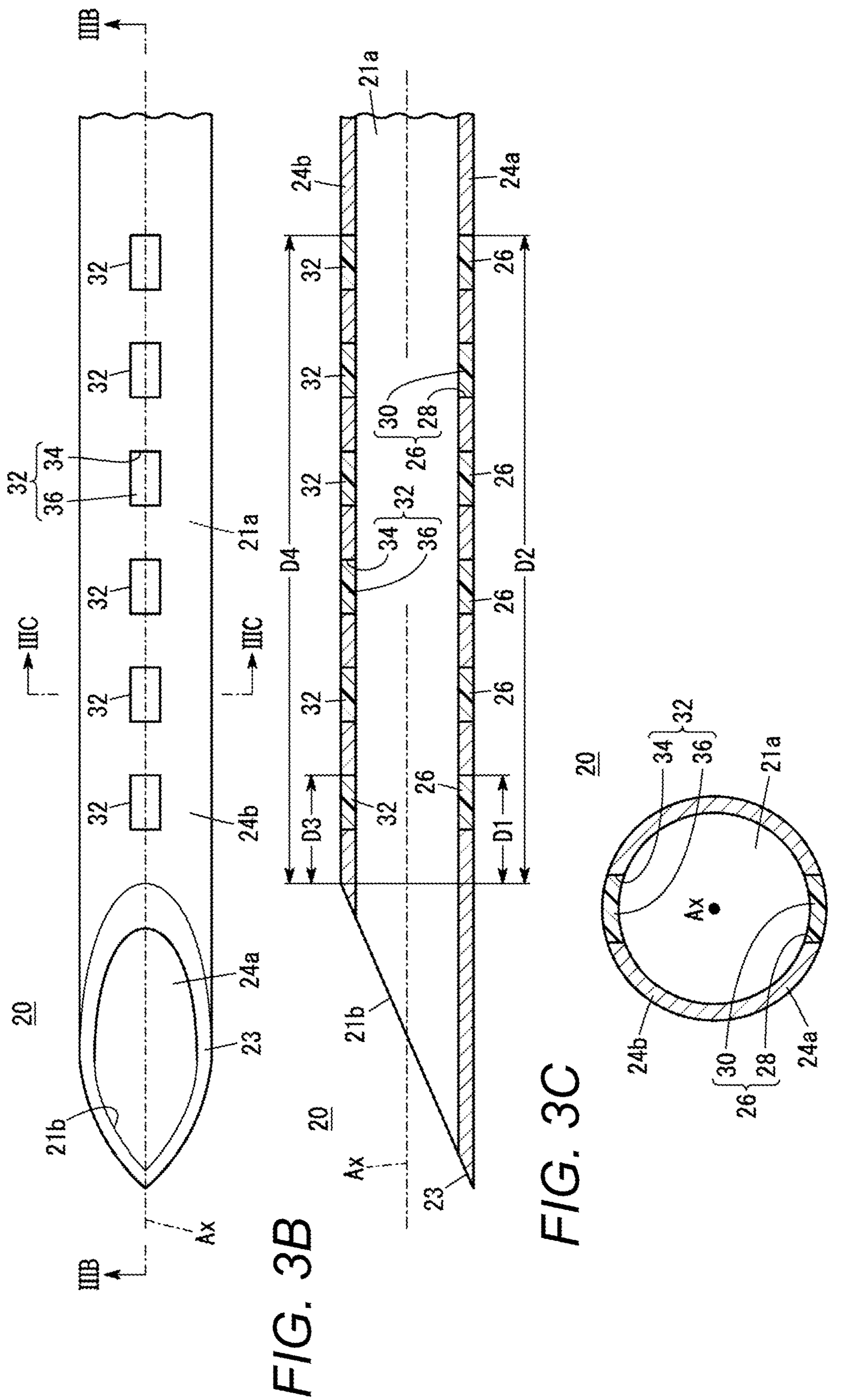
FIG. 3A is a plan view of a distal end portion of the needle body of FIG. 2.
FIG. 3B is a cross-sectional view taken along line IIIB-IIIB of FIG. 3A.
FIG. 3C is a cross-sectional view taken along line IIIC-IIIC of FIG. 3A.

In FIG. 2, the puncture needle 14 includes a needle body 20 made of metal and a needle hub 22 provided at a proximal end portion of the needle body 20. As illustrated in FIGS. 2 to 3C, the needle body 20 is a tubular member having rigidity and configured to puncture the skin 102 (see FIG. 4) of the patient. The needle body 20 has a lumen 21*a* extending along the axial direction. The needle body 20 is inserted into the lumen 16*a* of the catheter shaft 16 and a lumen 18*a* of the catheter hub 18 in the initial state (assembled state) of the catheter assembly 10 (see FIG. 1).

Examples of the metal material constituting the needle body 20 include stainless steel, aluminum, an aluminum alloy, titanium, and a titanium alloy. The needle body 20 is formed sufficiently longer than the catheter shaft 16 and protrudes from the distal end opening 16*b* of the catheter shaft 16 in the initial state of the catheter assembly 10 (see FIG. 1).

In FIGS. 3A and 3B, the needle body 20 at its distal end portion a blade surface 23 inclined with respect to an axis Ax of the needle body 20. The blade surface 23 has a distal end opening 21*b* communicating with the lumen 21*a* of the needle body 20.

As illustrated in FIGS. 3B and 3C, the needle body 20 includes a first wall portion 24*a* located below the axis Ax of the needle body 20 in the horizontal state (state of FIG. 3B) of the needle body 20 in which the axis Ax of the needle body 20 is located in the horizontal direction such that the blade surface 23 faces upward, and a second wall portion 24*b* located above the axis Ax of the needle body 20 in the horizontal state of the needle body 20. In FIG. 3C, the first wall portion 24*a* forms the lower half of the needle body 20 in the horizontal state of the needle body 20. The first wall portion 24*a* extends 180° in the circumferential direction of the needle body 20. The second wall portion 24*b* forms the upper half of the needle body 20 in the horizontal state of the needle body 20. The second wall portion 24*b* extends 180° in the circumferential direction of the needle body 20. Both end portions of the first wall portion 24*a* are integrally connected to both respective end portions of the second wall portion 24*b*.

As illustrated in FIGS. 3B and 3C, the first wall portion 24*a* has a plurality of (In the example of FIG. 3B, six) first transmission windows 26 at equal intervals along the axial direction of the needle body 20. The number of first transmission windows 26 is not limited to six, and may be one, or two or more (other than six). Each of the plurality of first transmission windows 26 is provided at a position located at the lowermost portion of the first wall portion 24*a* in the horizontal state of the needle body 20 (see FIG. 3C).

In FIG. 3B, the first transmission window 26 located on the most distal end side of the needle body 20 is located in the proximal direction relative to the proximal end of the blade surface 23. A distance D1 from the proximal end of the blade surface 23 to the proximal end of the first transmission window 26 located on the most distal end side of the needle body 20 is within 2 mm. In other words, the first transmission window 26 located on the most distal end side of the needle body 20 is located in a range within 2 mm in the proximal direction from the proximal end of the blade surface 23. Note that two or more first transmission windows 26 may be disposed in a range within 2 mm in the proximal direction from the proximal end of the blade surface 23 in the needle body 20.

A distance D2 from the proximal end of the blade surface 23 to the proximal end of the first transmission window 26 located on the most proximal end side of the needle body 20 is within 30 mm. In other words, all of the plurality of first transmission windows 26 is located in a range within 30 mm in the proximal direction from the proximal end of the blade surface 23. However, the first transmission window 26 may be provided at up to the proximal end portion of the needle body 20.

The plurality of first transmission windows 26 is formed to have the same size and the same shape. However, the plurality of first transmission windows 26 may be formed in different sizes or may be formed in different shapes. Each first transmission window 26 is formed in a quadrangular shape. The shape of each first transmission window 26 is not limited to the quadrangular shape.

Each of the first transmission windows 26 includes a first through hole 28 penetrating the first wall portion 24*a* and a first transmission member 30 disposed to close the first through hole 28. The first transmission member 30 is formed to be configured to transmit light L from the visualization device 13 (see FIG. 1). Specifically, the first transmission member 30 can transmit near-infrared light. The first transmission member 30 is made of, for example, a material such as glass or acrylic.

As illustrated in FIGS. 3A to 3C, the second wall portion 24*b* has a plurality of (six in the example of FIGS. 3A and 3B) second transmission windows 32 at equal intervals along the axial direction of the needle body 20. The number of second transmission windows 32 is not limited to six, and may be one, or two or more (other than six). In FIG. 3C, each of the plurality of second transmission windows 32 is provided at a position located at the uppermost portion of the second wall portion 24*b* in the horizontal state of the needle body 20. The first transmission window 26 and the second transmission window 32 face each other across the axis Ax of the needle body 20. In other words, the second transmission windows 32 are at a position shifted in phase by 180° in the circumferential direction of the needle body 20 with respect to the respective first transmission windows 26.

The second transmission window 32 located on the most distal end side of the needle body 20 is located in the proximal direction relative to the proximal end of the blade surface 23. A distance D3 from the proximal end of the blade surface 23 to the proximal end of the second transmission window 32 located on the most distal end side of the needle body 20 is 2 mm or less. In other words, the second transmission window 32 located on the most distal end side of the needle body 20 is located in a range within 2 mm in the proximal direction from the proximal end of the blade surface 23. Note that two or more second transmission windows 32 may be disposed in a range within 2 mm in the proximal direction from the proximal end of the blade surface 23 in the needle body 20.

A distance D4 from the proximal end of the blade surface 23 to the proximal end of the second transmission window 32 located on the most proximal end side of the needle body 20 is within 30 mm. In other words, all of the plurality of second transmission windows 32 are located in a range within 30 mm in the proximal direction from the proximal end of the blade surface 23. However, the second transmission window 32 may be provided at up to the proximal end portion of the needle body 20.

The plurality of second transmission windows 32 are formed to have the same size and the same shape. However, the plurality of second transmission windows 32 may be formed in different sizes or may be formed in different shapes. Each of the second transmission windows 32 is formed in a quadrangular shape. The shape of each second transmission window 32 is not limited to the quadrangular shape.

The size and shape of the second transmission window 32 are the same as the size and shape of the first transmission window 26. The size and shape of the second transmission window 32 may be different from the size and shape of the first transmission window 26. Each of the second transmission windows 32 includes a second through hole 34 penetrating the second wall portion 24*b* and a second transmission member 36 disposed to close the second through hole 34. The second transmission member 36 is formed to be configured to transmit light L (for example, near-infrared light) from the visualization device 13 (see FIG. 1). Specifically, the second transmission member 36 can transmit near-infrared light. The second transmission member 36 can be made of the same material as the first transmission member 30.

In FIGS. 1 and 2, the needle hub 22 is formed in a hollow shape (tubular shape). The constituent material of the needle hub 22 may be the same as the constituent material of the catheter hub 18 described above. A proximal end portion of the needle body 20 is fixed to a distal end portion of the needle hub 22. The needle hub 22 functions as an operation unit of the catheter assembly 10.

As illustrated in FIG. 1, the visualization device 13 includes an irradiation unit 40, a light receiving unit 42, and an image display unit 44. The irradiation unit 40 irradiates the living body 100 punctured with the needle body 20 with light L. The irradiation unit 40 includes a light source 46 that emits light L. The light L is near-infrared light. The near-infrared light includes, for example, wavelengths of 700 nm or more and 2500 nm or less, preferably 700 nm or more and 1400 nm or less, and more preferably 780 nm or more and 940 nm or less. Such light L is absorbed by blood and does not pass through the metal needle body 20. The light source 46 may emit visible light (not including near-infrared light). Furthermore, the light source 46 may emit light including both near-infrared light and visible light.

The light receiving unit 42 is disposed opposite the irradiation unit 40 with the living body 100 interposed therebetween. The light receiving unit 42 is a camera (imaging unit) that receives transmitted light of the light L with which the irradiation unit 40 irradiates the living body 100 punctured with the needle body 20 and images the living body 100 and the needle body 20. For example, the light receiving unit 42 includes a near-infrared CCD camera or the like. The image display unit 44 displays an image (transmitted light image 50) created based on the transmitted light received by the light receiving unit 42.

Next, a procedure of blood vessel puncture using the vascular puncture system 11 will be described.

As illustrated in FIG. 1, in the initial state of the catheter assembly 10, the blade surface 23 protrudes in the distal direction from the distal end opening 16*b* of the catheter shaft 16 in a state of facing upward.

Figure 4:
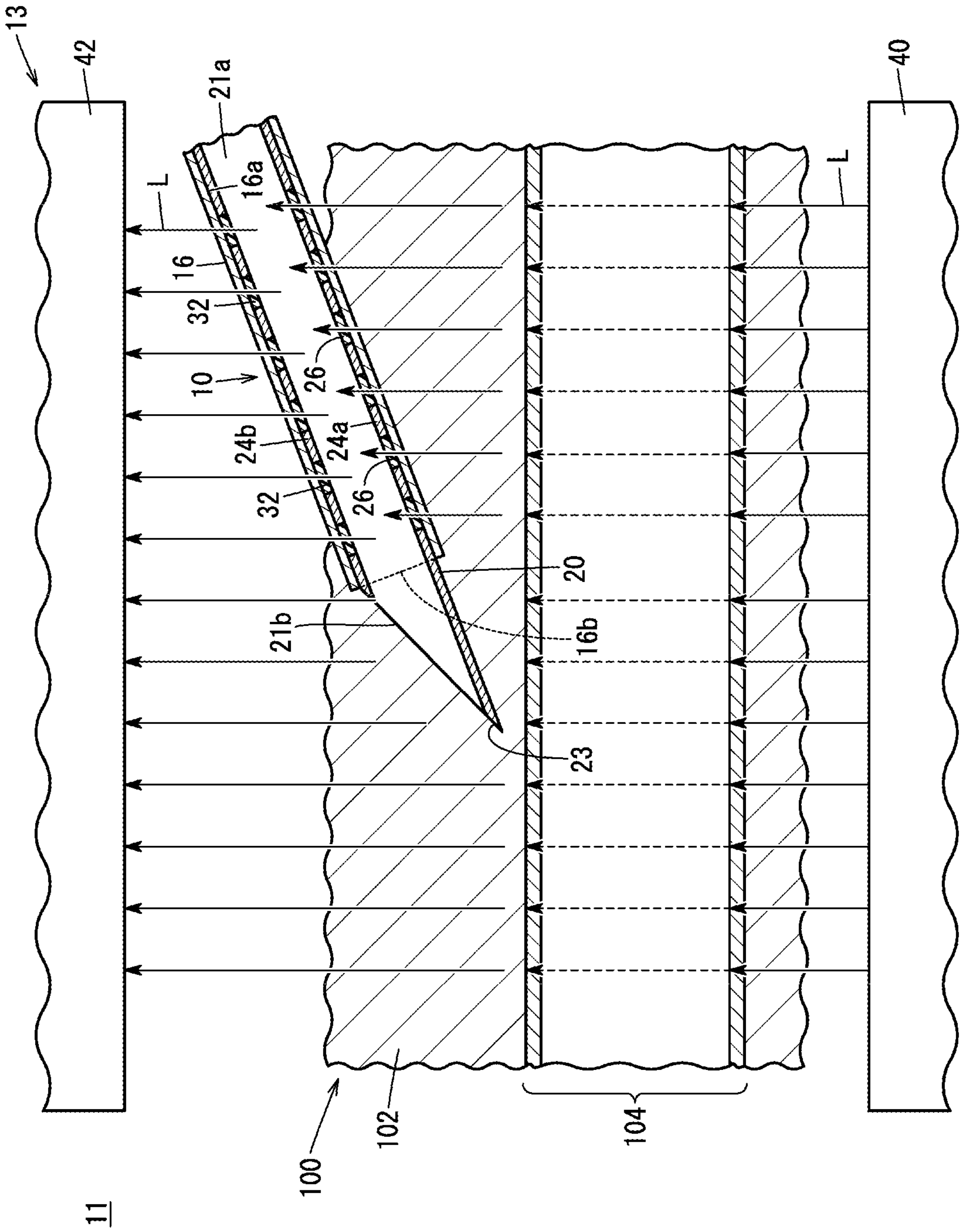
FIG. 4 is a first explanatory view of a puncture procedure for a blood vessel with the catheter assembly of FIG. 1.

First, the user sets the visualization device 13. Specifically, as illustrated in FIG. 4, the irradiation unit 40 is disposed below the living body 100 to be punctured, and the light receiving unit 42 is disposed above the living body 100 (see FIG. 1). Then, the irradiation unit 40 irradiates the living body 100 with the light L, and the living body 100 is punctured with the needle body 20 (distal end portion of the catheter assembly 10).

Figure 5:
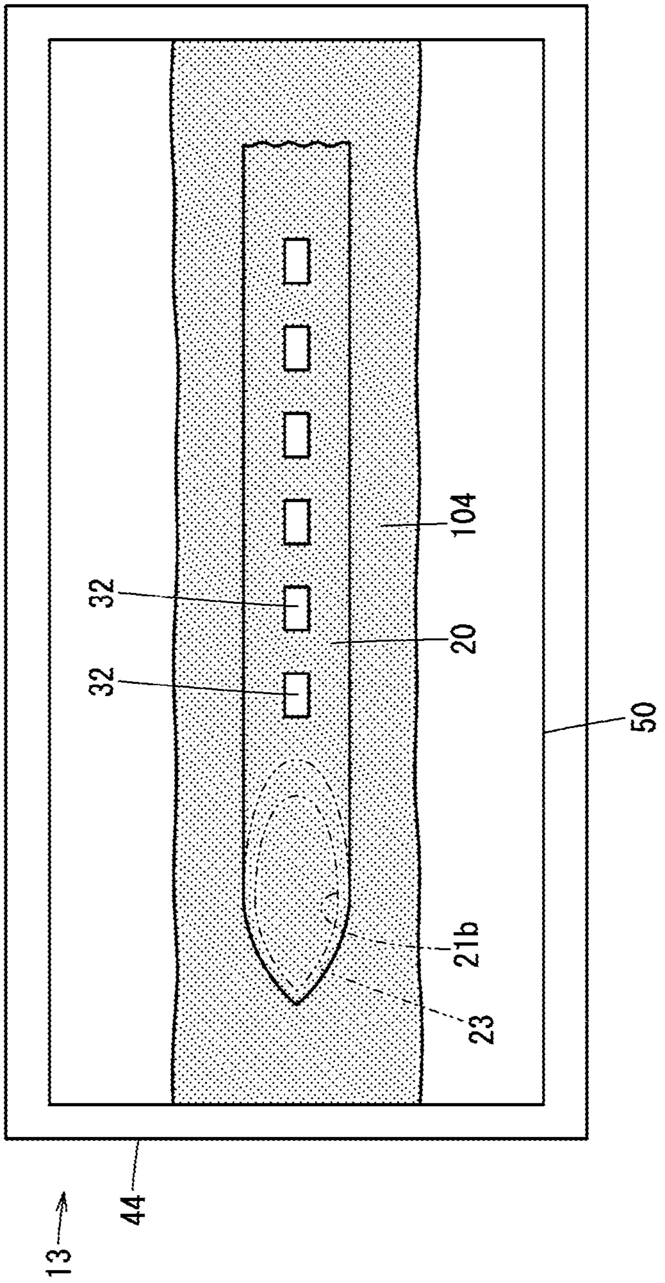
FIG. 5 is a transmitted light image in the state of FIG. 4.

Then, the light L emitted from the irradiation unit 40 is transmitted through the skin 102 of the living body 100 while being scattered. At this time, the light L is absorbed by blood (hemoglobin) in the blood vessel 104 of the living body 100. The light L is not transmitted through the needle body 20. Then, the light receiving unit 42 receives the transmitted light transmitted through the living body 100 among the light L. As a result, as illustrated in FIG. 5, the transmitted light image 50 created based on the transmitted light received by the light receiving unit 42 is displayed on the image display unit 44. The blood vessel 104 and the needle body 20 in the living body 100 are displayed on the transmitted light image 50. Specifically, in the transmitted light image 50, for example, the blood vessel 104 and the needle body 20 are displayed in black. In this case, because the color densities of the blood vessel 104 and the needle body 20 are different from each other, the user can distinguish the blood vessel 104 and the needle body 20 in the transmitted light image 50.

In FIG. 4, the light L scattered in the skin 102 is transmitted through the plurality of first transmission windows 26 provided in the needle body 20 and is guided to the lumen 21*a* of the needle body 20. Then, the light L guided to the lumen 21*a* of the needle body 20 is led to the outside of the living body 100 through the plurality of second transmission windows 32 and the skin 102, and received by the light receiving unit 42. Therefore, as illustrated in FIG. 5, the plurality of second transmission windows 32 is displayed (for example, second transmission window 32 is displayed in white) in the needle body 20 in the transmitted light image 50.

At this time, as illustrated in FIG. 4, when the blade surface 23 is located above (directly above) the blood vessel 104, blood does not flow into the lumen 21*a* of the needle body 20. Therefore, in the transmitted light image 50, all the second transmission windows 32 do not change (for example, all second transmission windows 32 remain displayed in white). As a result, the user can recognize that the needle body 20 is not located in the blood vessel (state in which the blade surface 23 is not located in the blood vessel 104) by visually recognizing the transmitted light image 50 (state in which the plurality of second transmission windows 32 is not changed).

Figure 6:
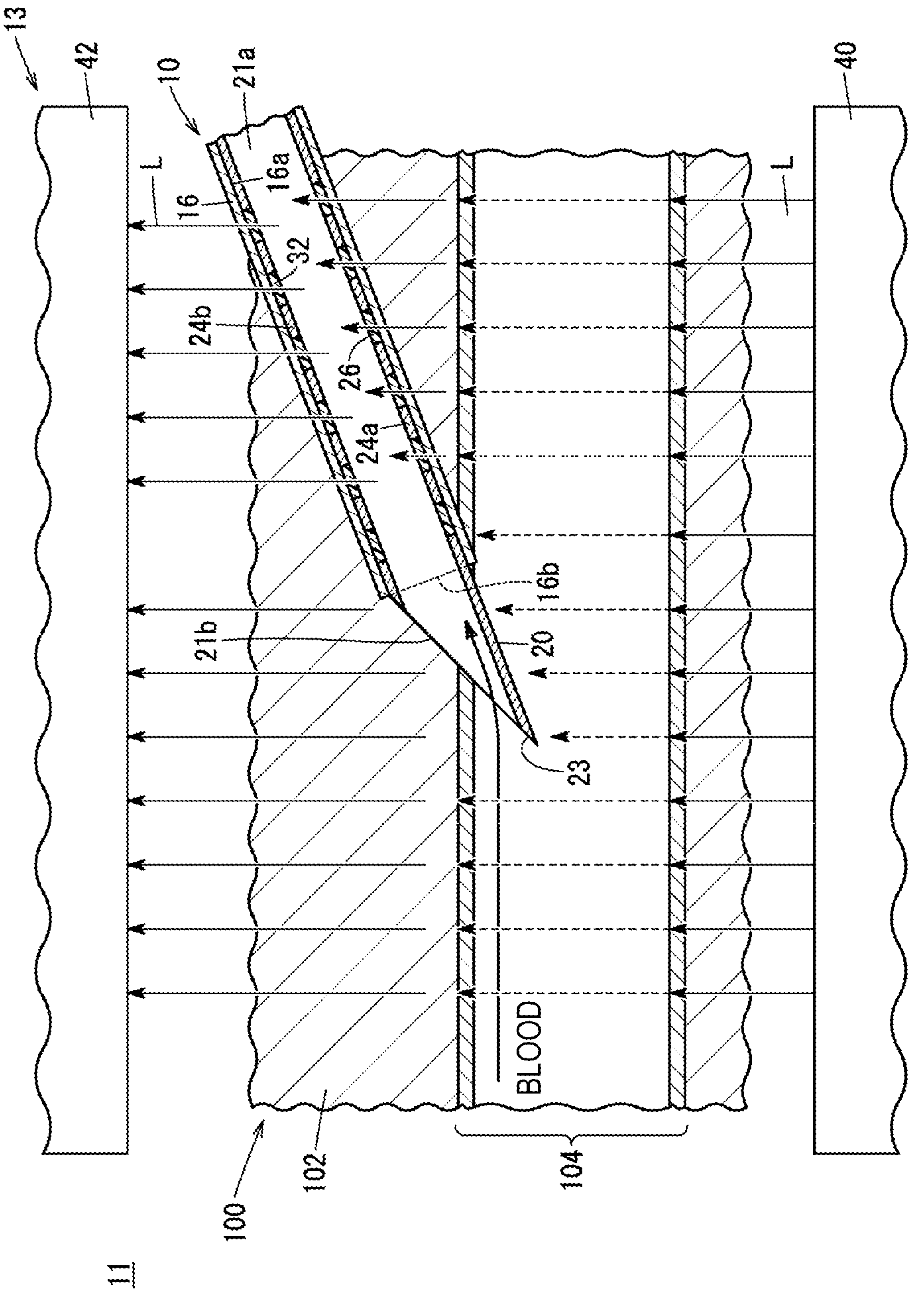
FIG. 6 is a second explanatory view of a puncture procedure for a blood vessel with the catheter assembly of FIG. 1.

Subsequently, for example, the user operates the catheter assembly 10 to adjust the position of the blade surface 23. Then, as illustrated in FIG. 6, when the blade surface 23 is inserted into the blood vessel 104, the blood in the blood vessel 104 flows from the distal end opening 21*b* of the needle body 20 into the lumen 21*a* of the needle body 20. When the second transmission window 32 located at the most distal end is covered with the blood in the lumen 21*a* of the needle body 20, the light L guided from the first transmission window 26 to the lumen 21*a* of the needle body 20 is absorbed by the blood before being guided to the second transmission window 32. Therefore, the light L in the lumen 21*a* of the needle body 20 is not led out from the second transmission window 32 located at the most distal end.

Figure 7:
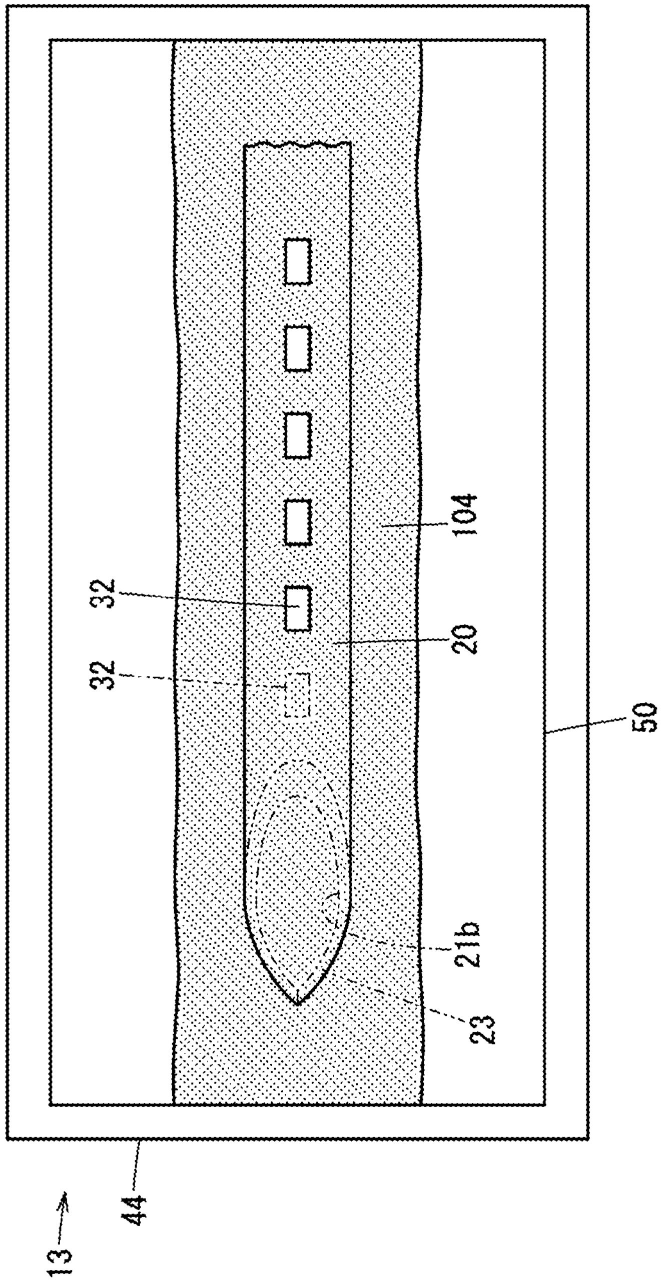
FIG. 7 is a transmitted light image in the state of FIG. 6.

Therefore, as illustrated in FIG. 7, the appearance of the second transmission window 32 located at the most distal end of the needle body 20 changes in the transmitted light image 50 (for example, the color changes from white to black). In other words, in the transmitted light image 50, the second transmission window 32 located at the most distal end of the needle body 20 cannot be seen (Alternatively, it is difficult to see). In the transmitted light image 50, the appearance of the plurality of second transmission windows 32 changes in order from the distal end side to the proximal end side as the blood is guided to the proximal end side of the lumen 21*a* of the needle body 20. Therefore, the user can recognize that the needle body 20 is located in the blood vessel at an early stage before the blood is guided to the needle hub 22 by visually recognizing the transmitted light image 50.

After the needle body 20 is located in the blood vessel, the user removes the puncture needle 14 in a state in which the distal end portion of the catheter shaft 16 is indwelled in the blood vessel 104, and administers a drug into the blood vessel 104 via the catheter.

The puncture needle 14, the catheter assembly 10, and the vascular puncture system 11 according to the present embodiment have the following effects.

The needle body 20 includes the blade surface 23 formed at the distal end portion of the needle body 20, the first transmission windows 26 configured to transmit the light L, and the second transmission windows 32 configured to transmit the light L transmitted through the first transmission window 26. The second transmission window 32 is located on a proximal end side relative to the blade surface 23, and the first transmission window 26 and the second transmission window 32 are located to be shifted from each other in the circumferential direction of the needle body 20.

According to such a configuration, the light L with which the living body 100 punctured with the needle body 20 is irradiated is transmitted through the first transmission window 26 and is guided to the lumen 21*a* of the needle body 20. When the needle body 20 is not located in the blood vessel and the blood does not flow into the lumen 21*a* of the needle body 20, the light L guided from the first transmission window 26 to the lumen 21*a* of the needle body 20 is transmitted through the second transmission window 32 and is led to the outside of the needle body 20.

Therefore, the user can visually recognize the second transmission window 32 in the needle body 20 in the transmitted light image 50.

On the other hand, when the needle body 20 is located in the blood vessel and the blood flowing into the lumen 21*a* of the needle body 20 covers the second transmission window 32, the light L guided from the first transmission window 26 to the lumen 21*a* of the needle body 20 is absorbed by the blood and thus is not transmitted through the second transmission window 32. Therefore, in the transmitted light image 50, the appearance of the second transmission window 32 of the needle body 20 changes (the second transmission window 32 is invisible or the second transmission window 32 is difficult to see). Therefore, the user can recognize that the needle body 20 is located in the blood vessel based on the transmitted light image 50.

The blade surface 23 is inclined with respect to the axis Ax of the needle body 20. The needle body 20 includes the first wall portion 24*a* located below the axis Ax of the needle body 20 in the horizontal state of the needle body 20 in which the axis Ax of the needle body 20 is located in the horizontal direction such that the blade surface 23 faces upward, and the second wall portion 24*b* located above the axis Ax of the needle body 20 in the horizontal state. The first transmission window 26 is provided in the first wall portion 24*a*, and the second transmission window 32 is provided in the second wall portion 24*b*.

According to such a configuration, the light L introduced from the first transmission window 26 into the lumen 21*a* of the needle body 20 can be led out from the second transmission window 32.

A plurality of second transmission windows 32 is provided.

According to such a configuration, a change in the second transmission window 32 can be easily seen in the transmitted light image 50.

At least one second transmission window 32 is provided in a range of 2 mm in the proximal direction from the proximal end of the blade surface 23 in the axial direction of the needle body 20.

According to such a configuration, it is possible to change the appearance of the second transmission window 32 of the transmitted light image 50 at a relatively early stage after the blood is introduced from the distal end opening 21*b* of the needle body 20 into the lumen 21*a* of the needle body 20.

Each of the first transmission window 26 and the second transmission window 32 can transmit near-infrared light.

According to such a configuration, the blood vessel 104 and the needle body 20 can be clearly displayed in the transmitted light image 50.

The first transmission window 26 includes the first through hole 28 formed in the needle body 20 and the first transmission member 30 disposed so as to close the first through hole 28. The second transmission window 32 includes the second through hole 34 formed in the needle body 20 and the second transmission member 36 disposed so as to close the second through hole 34.

According to such a configuration, the blood in the lumen 21*a* of the needle body 20 can be suppressed from flowing to the outside of the needle body 20 from the first transmission window 26 and the second transmission window 32, and the strength of the needle body 20 can be secured.

The vascular puncture system 11 includes the puncture needle 14, an irradiation unit 40 for irradiating the living body 100 punctured with the needle body 20 with the light L, and the light receiving unit 42 for receiving transmitted light transmitted through the living body 100.

According to such a configuration, the transmitted light image 50 can be obtained by the irradiation unit 40 and the light receiving unit 42.

First Modification

Next, a needle body 20*a* according to a first modification of the present invention will be described. In the needle body 20*a* according to the present modification, the same components as those of the needle body 20 described above are denoted by the same reference numerals, and a detailed description thereof will be omitted. In addition, in the needle body 20*a* according to the present modification, the same configuration as the above-described needle body 20 has the same effect. The same applies to needle bodies 20*b* to 20*h* according to second to eighth modifications described later.

Figure 8A:
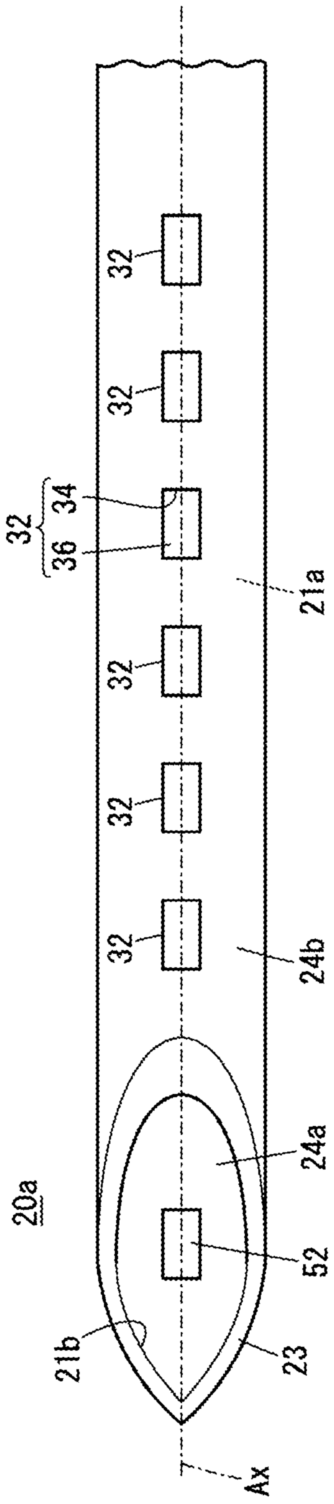
FIG. 8A is a plan view of a needle body according to a first modification.

As illustrated in FIG. 8A, a third transmission window 52 configured to transmit the light L is provided at a portion, of the first wall portion 24*a* of the needle body 20*a*, facing the distal end opening 21*b* of the needle body 20*a*. In other words, the third transmission window 52 overlaps the distal end opening 21*b* of the needle body 20*a* in top view of the needle body 20*a* in the horizontal state of the needle body 20*a*. The third transmission window 52 is provided at a position located at the lowermost portion of the first wall portion 24*a* in the horizontal state of the needle body 20*a*. The third transmission window 52 is configured as in the first transmission window 26 and the second transmission window 32. The shape and size of the third transmission window 52 are formed to be the same as the shape and size of the first transmission window 26 described above. However, the shape and size of the third transmission window 52 can be appropriately changed.

In the present modification, the blade surface 23 has a distal end opening 21*b* communicating with the lumen 21*a* of the needle body 20*a*. The third transmission window 52 configured to transmit the light L is provided at a portion, of the first wall portion 24*a*, facing the distal end opening 21*b*.

According to such a configuration, the light L guided to the lumen 21*a* of the needle body 20*a* through the third transmission window 52 can be led out from the distal end opening 21*b* of the needle body 20*a*. As a result, it is possible to recognize that the needle body 20*a* is located in the blood vessel at an earlier stage.

Second Modification

Figure 8B:
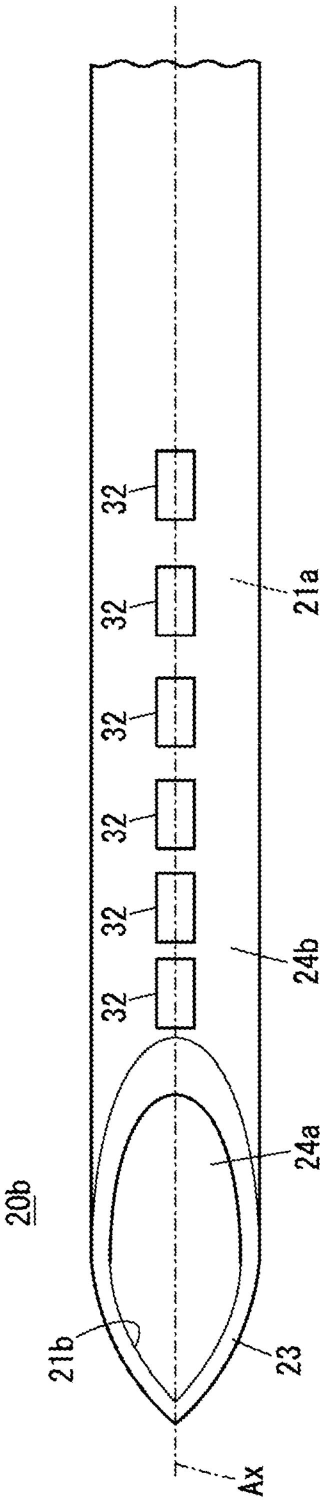
FIG. 8B is a plan view of a needle body according to a second modification.

Next, a needle body 20*b* according to a second modification of the present invention will be described. As illustrated in FIG. 8B, in the needle body 20*b*, the distance between the second transmission windows 32 adjacent to each other on the distal end side of the needle body 20*b* is narrower than the distance between the second transmission windows 32 adjacent to each other on the proximal end side of the needle body 20*b*. In other words, the distance between the second transmission windows 32 adjacent to each other gradually increases from the distal end side toward the proximal end side.

According to such a configuration, it is possible to easily visually recognize the change in the second transmission window 32 in the transmitted light image 50 at the initial stage when the blood flows into the lumen 21*a* of the needle body 20*b*. As a result, it is possible to effectively allow a user to recognize that the needle body 20*b* is located in the blood vessel at an early stage.

Third Modification

Figures 9A, 9B, 9C:
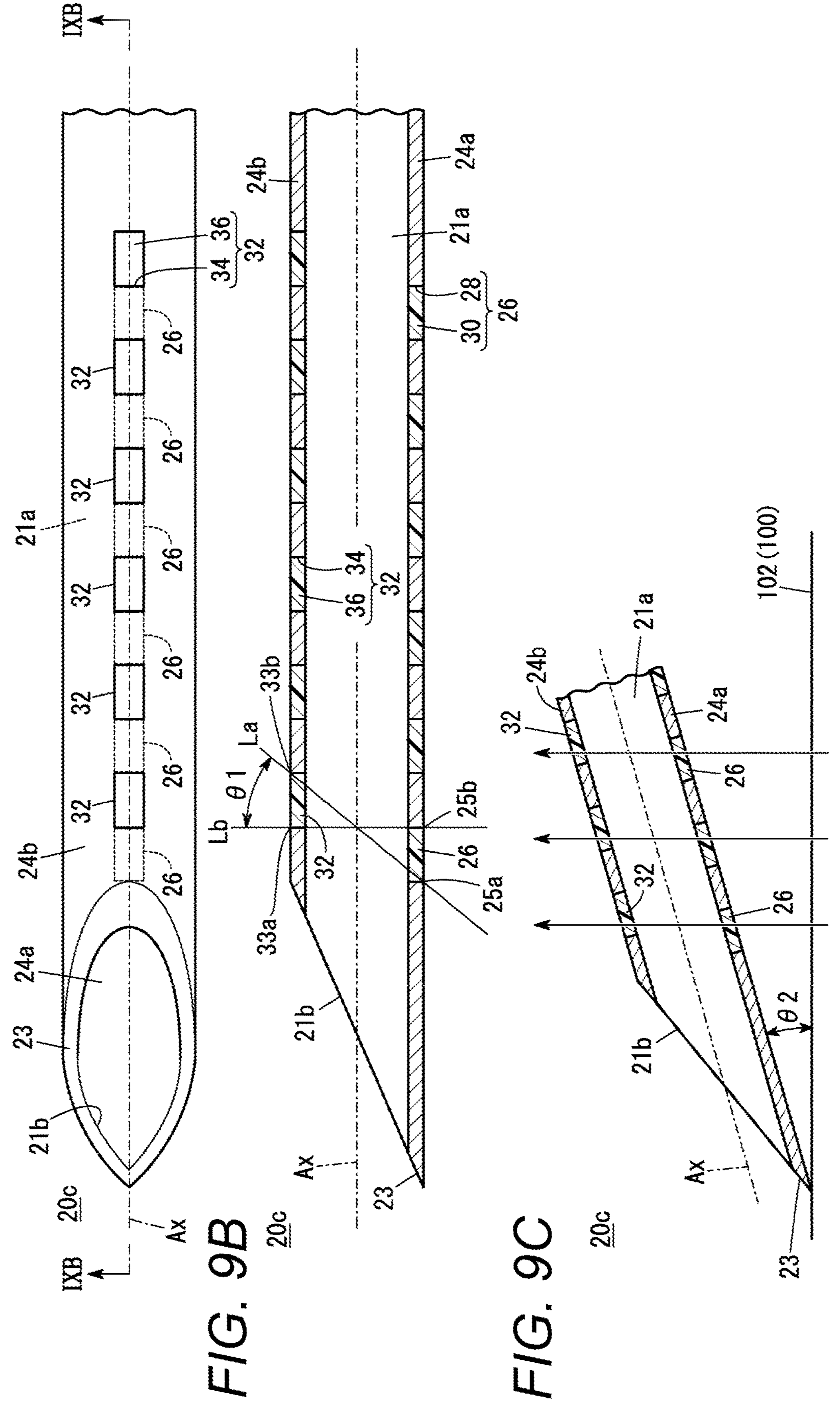
FIG. 9A is a plan view of a needle body according to a third modification.
FIG. 9B is a cross-sectional view taken along line IXB-IXB of FIG. 9A.
FIG. 9C is an explanatory view illustrating a state in which the needle body of FIG. 9B is inclined by a predetermined puncture angle.

Next, a needle body 20*c* according to a third modification of the present invention will be described. As illustrated in FIGS. 9A and 9B, in the needle body 20*c*, the second transmission window 32 is disposed to be shifted by a predetermined distance to the proximal end side of the needle body 20*c* with respect to the first transmission window 26. In FIG. 9B, the first transmission window 26 includes a first distal end 25*a* and a first proximal end 25*b*. The second transmission window 32 includes a second distal end 33*a* located at the distal end of the needle body 20*c* in the axial direction and a second proximal end 33*b* located at the proximal end of the needle body 20*c* in the axial direction. In the first transmission window 26 and the second transmission window 32 close to each other, the second proximal end 33*b* is located on the proximal end side of the needle body 20*c* relative to the first proximal end 25*b*.

In the first transmission window 26 and the second transmission window 32 close to each other, an angle θ1 formed by a first line segment La connecting the first distal end 25*a* and the second proximal end 33*b* and a second line segment Lb connecting the first proximal end 25*b* and the second distal end 33*a* is 10° or more and 45° or less.

In this case, as illustrated in FIG. 9C, when the needle body 20*c* punctures the living body 100 (skin 102) at a puncture angle θ2 (an angle formed by the skin 102 and the needle body 20*c*) of 10° or more and 45° or less, the light L transmitted through the first transmission window 26 from below to above is transmitted through the second transmission window 32 as it is without being reflected by the inner peripheral surface of the needle body 20*c*. Note that the angle θ1 can be appropriately changed according to the puncture angle θ2, and may be, for example, 15° or more and 30° or less.

In the present modification, the first transmission window 26 is provided at a position located at the lowermost portion of the first wall portion 24*a* in the horizontal state of the needle body 20*c*, and the second transmission window 32 is provided at a position located at the uppermost portion of the second wall portion 24*b* in the horizontal state of the needle body 20*c*. The first transmission window 26 includes the first distal end 25*a* located at the distal end of the needle body 20*c* in the axial direction and the first proximal end 25*b* located at the proximal end of the needle body 20*c* in the axial direction.

The second transmission window 32 includes the second distal end 33*a* located at the distal end of the needle body 20*c* in the axial direction and the second proximal end 33*b* located at the proximal end of the needle body 20*c* in the axial direction. The second proximal end 33*b* is located on the proximal end side of the needle body 20*c* relative to the first proximal end 25*b*. An angle formed by the first line segment La connecting the first distal end 25*a* and the second proximal end 33*b* and the second line segment Lb connecting the first proximal end 25*b* and the second distal end 33*a* is 10° or more and 45° or less.

According to such a configuration, in a state in which the living body 100 is punctured with the needle body 20*c* at the puncture angle of 10° or more and 45° or less, the light L transmitted from below to above through the first transmission window 26 can be guided to the second transmission window 32 as it is without being reflected by the inner peripheral surface of the needle body 20*c*. As a result, the second transmission window 32 can be displayed more clearly in the transmitted light image 50.

Fourth Modification

Figures 10A, 10B, 10C:
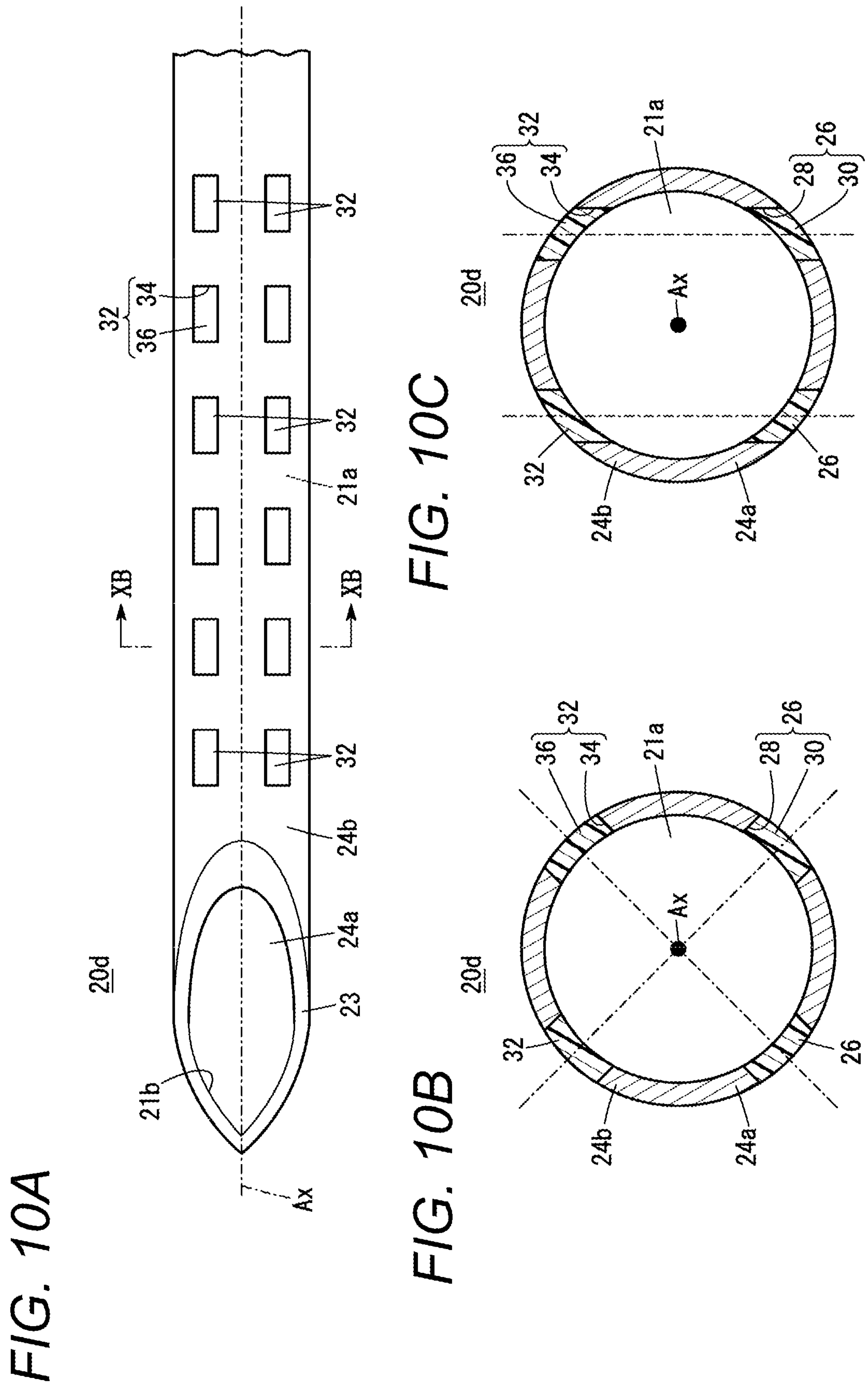
FIG. 10A is a plan view of a needle body according to a fourth modification.
FIG. 10B is a cross-sectional view taken along line XB-XB in FIG. 10A.
FIG. 10C is a cross-sectional view illustrating another configuration of the first transmission window and the second transmission window in FIG. 10B.

Next, a needle body 20*d* according to a fourth modification of the present invention will be described. As illustrated in FIGS. 10A and 10B, in the needle body 20*d*, the first transmission windows 26 and the second transmission windows 32 are each disposed in two rows at equal intervals in the axial direction of the needle body 20*d*. That is, as illustrated in FIG. 10B, the two first transmission windows 26 adjacent to each other in the circumferential direction of the needle body 20*d* are located so as to sandwich the lowermost portion of the first wall portion 24*a* in the horizontal state of the needle body 20*d*. Each of the first transmission windows 26 is formed such that the center line of the first transmission window 26 passes through the axis Ax of the needle body 20*d*.

The two second transmission windows 32 adjacent to each other in the circumferential direction of the needle body 20*d* are located so as to sandwich the uppermost portion of the second wall portion 24*b*. That is, the two second transmission windows 32 adjacent to each other in the circumferential direction of the needle body 20*d* are located so as to sandwich the uppermost portion of the second wall portion 24*b* in the horizontal state of the needle body 20*d*. Each of the second transmission windows 32 is formed such that the center line of the second transmission window 32 passes through the axis Ax of the needle body 20*d*.

One second transmission window 32 of the two second transmission windows 32 disposed in the circumferential direction of the needle body 20*d* faces one first transmission window 26 of the two first transmission windows 26 disposed in the circumferential direction of the needle body 20*d* across the axis Ax of the needle body 20*d*. The other second transmission window 32 of the two second transmission windows 32 disposed in the circumferential direction of the needle body 20*d* faces the other first transmission window 26 of the two first transmission windows 26 disposed in the circumferential direction of the needle body 20*d* across the axis Ax of the needle body 20*d*.

According to such a configuration, the change in the second transmission window 32 can be more easily visually recognized in the transmitted light image 50.

In the needle body 20*d*, the first transmission window 26 and the second transmission window 32 may be formed as illustrated in FIG. 10C. That is, as illustrated in FIG. 10C, the center line of one first transmission window 26 of the two first transmission windows 26 disposed in the circumferential direction of the needle body 20*d* extends in the vertical direction in the horizontal state of the needle body 20*d* and matches the center line of one second transmission window 32 of the second transmission windows 32 disposed in the circumferential direction of the needle body 20*d*. The center line of the other first transmission window 26 of the two second transmission windows 32 disposed in the circumferential direction of the needle body 20*d* extends in the vertical direction in the horizontal state of the needle body 20*d* and matches the center line of the other second transmission window 32 of the second transmission windows 32 disposed in the circumferential direction of the needle body 20*d*.

Note that the first transmission windows 26 and the second transmission windows 32 are not limited to be disposed in two rows, and may be disposed at equal intervals in the axial direction of the needle body 20*d* in three or more rows.

Fifth Modification

Figure 11A:
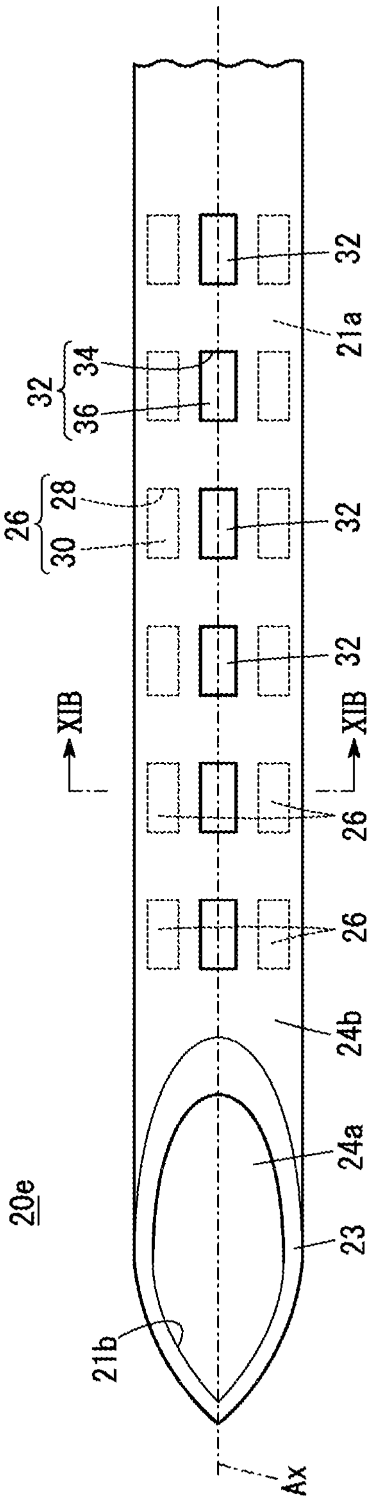
FIG. 11A is a plan view of a needle body according to a fifth modification.
Figure 11B:
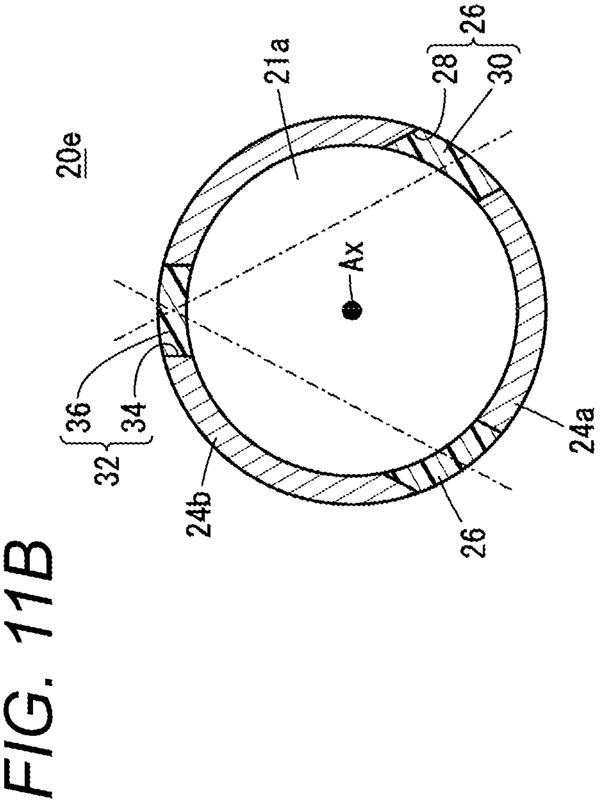
FIG. 11B is a cross-sectional view taken along line XIB-XIB of FIG. 11A.

Next, a needle body 20*e* according to a fifth modification of the present invention will be described. As illustrated in FIGS. 11A and 11B, in the needle body 20*e*, the plurality of first transmission windows 26 is disposed at equal intervals in the axial direction of the needle body 20*e* in a state of being disposed in two rows. That is, as illustrated in FIG. 11B, the two first transmission windows 26 adjacent to each other in the circumferential direction of the needle body 20*e* are located so as to sandwich the lowermost portion of the first wall portion 24*a* in the horizontal state of the needle body 20*e*.

The second transmission window 32 is located at a portion that is the uppermost portion of the second wall portion 24*b* in the horizontal state of the needle body 20*e*. The center line of each first transmission window 26 passes through the second transmission window 32 (the center of the second transmission window 32).

According to such a configuration, the light L can be efficiently guided from the plurality of first transmission windows 26 to the lumen 21*a* of the needle body 20*e*.

Sixth Modification

Figure 12A:
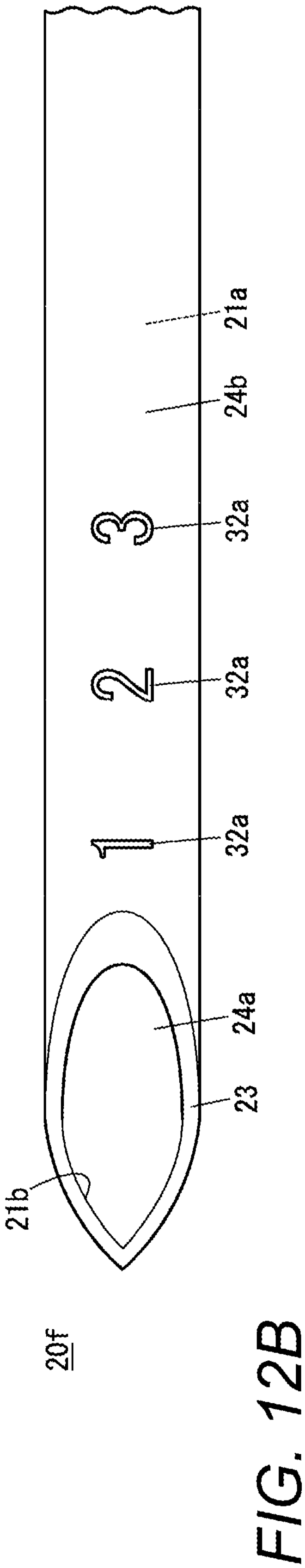
FIG. 12A is a plan view of a needle body according to a sixth modification.

Next, a needle body 20*f* according to a sixth modification of the present invention will be described. As illustrated in FIG. 12A, in the needle body 20*f*, a plurality of (three in FIG. 12A) second transmission windows 32*a* is formed in an Arabic figure shape. The second transmission window 32*a* is formed so as to be disposed in the order of 1, 2, and 3 from the distal end side toward the proximal end side of the needle body 20*f*. However, the number of second transmission windows 32*a* may be two or four or more. In addition, the arrangement and orientation of the numbers can be changed as appropriate. Furthermore, the second transmission window 32*a* may be displayed with Roman numerals, Greek numerals, or the like.

The plurality of second transmission windows 32*a* is different from each other in shape.

According to such a configuration, a change in the second transmission window 32*a* can be easily seen in the transmitted light image 50.

Seventh Modification

Figure 12B:
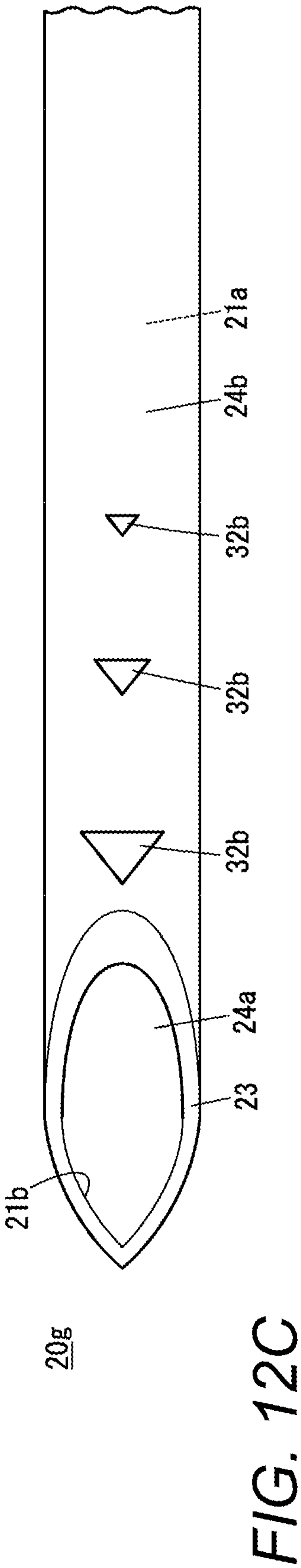
FIG. 12B is a plan view of a needle body according to a seventh modification.

Next, a needle body 20*g* according to a seventh modification of the present invention will be described. As illustrated in FIG. 12B, in the needle body 20*g*, each of the second transmission windows 32*b* is formed in a triangular shape (regular triangular shape). One side of the triangle of the second transmission window 32*b* extends along the circumferential direction of the needle body 20*g*. The size of the second transmission window 32*b* gradually decreases from the distal end side toward the proximal end side of the needle body 20*g*. However, the sizes of the plurality of second transmission windows 32*b* may be the same. The shape of the second transmission window 32*b* is not limited to the triangular shape, and may be a circular shape, an arrow shape, or the like.

The plurality of second transmission windows 32*b* are different from each other in size.

According to such a configuration, a change in the second transmission window 32*b* can be easily seen in the transmitted light image 50.

Eighth Modification

Figure 12C:
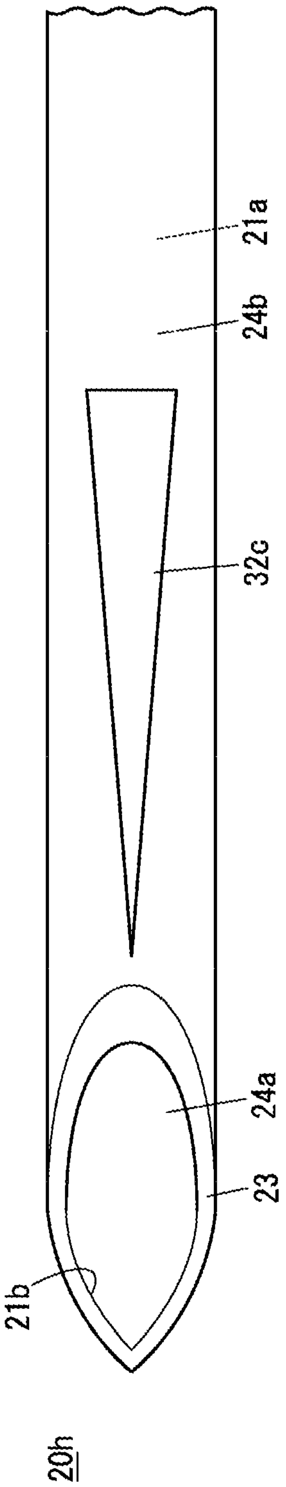
FIG. 12C is a plan view of a needle body according to an eighth modification.

Next, a needle body 20*h* according to an eighth modification of the present invention will be described. As illustrated in FIG. 12C, in the needle body 20*h*, only one second transmission window 32*c* is provided. The second transmission window 32*c* is formed in a triangular shape (isosceles triangular shape). One side of the triangle of the second transmission window 32*c* extends along the circumferential direction of the needle body 20*h*. The width of the second transmission window 32*c* in the circumferential direction of the needle body 20*h* gradually increases from the distal end side toward the proximal end side of the needle body 20*h*. The shape of the second transmission window 32*c* is not limited to the triangular shape, and may be a quadrangular shape, an elliptical shape, or the like.

The present invention is not limited to the above-described embodiments, and various modifications can be made without departing from the gist of the present invention. The first transmission window 26 may be formed only of the first through hole 28 without the first transmission member 30. Each of the second transmission windows 32 and 32*a* to 32*c* may be formed only of the second through hole 34 without the second transmission member 36.

The above embodiments are summarized as follows.

The above embodiments are directed to a medical puncture needle (14) includes a metal needle body (20, 20*a* to 20*h*) formed in a tubular shape, in which the needle body includes a blade surface (23) formed at a distal end portion of the needle body, a first transmission window (26) configured to transmit light (L), and a second transmission window (32, 32*a* to 32*c*) configured to transmit light transmitted through the first transmission window, the second transmission window is located on a proximal end side relative to the blade surface, and the first transmission window and the second transmission window are shifted from each other in a circumferential direction of the needle body.

In the above-described puncture needle, the blade surface may be inclined with respect to an axis (Ax) of the needle body, the needle body may include a first wall portion (24*a*) positioned below an axis of the needle body in a horizontal state of the needle body in which the axis of the needle body is positioned in a horizontal direction such that the blade surface faces upward, and a second wall portion (24*b*) positioned above the axis of the needle body in the horizontal state, the first transmission window may be provided in the first wall portion, and the second transmission window may be provided in the second wall portion.

In the above-described puncture needle, a plurality of the second transmission windows may be provided.

In the above-described puncture needle the plurality of second transmission windows is different from each other in at least one of a shape and a size.

In the above-described puncture needle, the blade surface may have a distal end opening (21*b*) communicating with a lumen (21*a*) of the needle body, and a third transmission window (52) configured to transmit light may be provided in a portion, of the first wall portion, facing the distal end opening.

In the above-described puncture needle, at least one of the second transmission windows may be provided in a range of 2 mm in the proximal direction from the proximal end of the blade surface in the axial direction of the needle body.

In the above-described puncture needle, each of the first transmission window and the second transmission window may transmit near-infrared light.

In the above-described puncture needle, the first transmission window may be provided at a position located at a lowermost portion of the first wall portion in the horizontal state of the needle body, the second transmission window may be provided at a position located at an uppermost portion of the second wall portion in the horizontal state of the needle body, the first transmission window may include a first distal end (25*a*) located at a distal end of the needle body in the axial direction, and a first proximal end (25*b*) located at a proximal end of the needle body in the axial direction, the second transmission window may include a second distal end (33*a*) located at a distal end of the needle body in the axial direction, and a second proximal end (33*b*) located at a proximal end of the needle body in the axial direction, the second proximal end may be located on a proximal end side of the needle body relative to the first proximal end, and an angle (θ1) formed by a first line segment (La) connecting the first distal end and the second proximal end and a second line segment (Lb) connecting the first proximal end and the second distal end may be 10° or more and 45° or less.

In the above-described puncture needle, each of the first transmission window and the second transmission window may include a through hole (28, 34) formed in the needle body, and a transmission member (30, 36) disposed to close the through hole.

According to another embodiment, a catheter assembly (10) includes the above-described puncture needle and a catheter shaft (16) having a lumen (16*a*) through which the needle body is inserted.

The above embodiments are directed to a vascular puncture system (11) including the above-described puncture needle, an irradiation unit (40) for irradiating a living body (100) punctured with the needle body with the light, and a light receiving unit (42) for receiving transmitted light having transmitted through the living body.

What is claimed is:

1. A vascular puncture system comprising:
- a medical puncture needle comprising:
  - a metal needle body formed in a tubular shape and comprising:
    - a blade surface formed at a distal end portion of the needle body,
    - a first transmission window configured to transmit light, and
    - a second transmission window configured to transmit light transmitted through the first transmission window, wherein:
    - the second transmission window is located on a proximal end side relative to the blade surface, and
    - the first transmission window and the second transmission window are shifted from each other in a circumferential direction of the needle body;
  - an irradiation unit configured to irradiate a living body punctured with the needle body with the light; and a light receiving unit configured to receive light transmitted through the living body.

2. A medical puncture needle comprising:

a metal needle body formed in a tubular shape and comprising:

a blade surface formed at a distal end portion of the needle body, a first transmission window configured to transmit light, and a second transmission window configured to transmit light transmitted through the first transmission window, wherein:

the second transmission window is located on a proximal end side relative to the blade surface, and the first transmission window and the second transmission window are shifted from each other in a circumferential direction of the needle body, and each of the first transmission window and the second transmission window comprises:

a through hole formed in the needle body, and a transmission member disposed to close the through hole.

3. The puncture needle according to claim 2, wherein:

the blade surface is inclined with respect to an axis of the needle body; and the needle body comprises:

a first wall portion located below an axis of the needle body in a horizontal state of the needle body in which the axis of the needle body is located in a horizontal direction such that the blade surface faces upward, and a second wall portion located above the axis of the needle body in the horizontal state, wherein:

the first transmission window is provided in the first wall portion, and the second transmission window is provided in the second wall portion.

4. The puncture needle according to claim 3, wherein:

a distance from a proximal end of the blade surface to a proximal end of the second transmission window is 2 mm or less.

5. The puncture needle according to claim 3, wherein:

the first transmission window is provided at a position located at a lowermost portion of the first wall portion in the horizontal state of the needle body;

the second transmission window is provided at a position located at an uppermost portion of the second wall portion in the horizontal state of the needle body;

a proximal end of the second transmission window is located proximal of a proximal end of the first transmission window, and an angle formed by a first line segment connecting a distal end of the first transmission window and the proximal end of the second transmission window and a second line segment connecting the proximal end of the first transmission window and a distal end of the second transmission window is 10° or more and 45° or less.

6. The puncture needle according to claim 2, wherein:

a plurality of the second transmission windows are provided.

7. The puncture needle according to claim 6, wherein:

the plurality of second transmission windows are different from each other in at least one of a shape or a size.

8. The puncture needle according to claim 2, wherein:

the blade surface has a distal end opening communicating with a lumen of the needle body, and a third transmission window configured to transmit light is provided at a portion of the first wall portion facing the distal end opening.

9. The puncture needle according to claim 2, wherein:

each of the first transmission window and the second transmission window is configured to transmit near-infrared light.

* * * * *